United States Patent [19]
Heilman et al.

[11] 3,957,664
[45] May 18, 1976

[54] LUBRICANT AND HYDRAULIC FLUID COMPOSITIONS

[75] Inventors: William J. Heilman, Allison Park; Thomas J. Lynch, Harmar Twp., both of Pa.

[73] Assignee: Gulf Research & Development Company, Pittsburgh, Pa.

[22] Filed: Dec. 12, 1974

[21] Appl. No.: 532,157

Related U.S. Application Data

[62] Division of Ser. No. 274,319, July 24, 1972, Pat. No. 3,876,720.

[52] U.S. Cl. ............................. 252/59; 260/677 R; 260/683.15 B
[51] Int. Cl.² ........................................... C10M 1/16
[58] Field of Search... 252/59; 260/677 R, 683.15 B

[56] References Cited
UNITED STATES PATENTS

| | | | |
|---|---|---|---|
| 3,382,291 | 5/1968 | Brennan | 260/683.15 B |
| 3,576,898 | 4/1971 | Blake et al. | 260/676 |
| 3,798,284 | 3/1974 | Tesei et al. | 252/59 X |
| 3,836,596 | 9/1974 | Driscoll | 260/683.15 B |
| 3,842,134 | 10/1974 | Pratt | 260/683.15 B |

*Primary Examiner*—Delbert E. Gantz
*Assistant Examiner*—Andrew H. Metz

[57] ABSTRACT

A novel composition of an internal olefin or mixture of internal olefins having the formula $R-(CH_2)_2-C(R)=CH-C(R)(CH_3)-(CH_2)_2-R$, where each R group is an alkyl group having from four to 12 carbon atoms and a minor amount of a lubricating oil anti-oxidant. A composition of 11,13-dioctyl-13-methyl-11-tricosene and two percent 2,6-di-t-butyl-p-cresol is useful as a high temperature lubricant.

6 Claims, No Drawings

LUBRICANT AND HYDRAULIC FLUID COMPOSITIONS

This patent application is a division of our patent application Ser. No. 274,319, filed July 24, 1972 and now U.S. Pat. No. 3,876,720.

This invention relates to compositions including one or more unsaturated olefinic dimers of vinylidene compounds and at least one additive including a lubricating oil anti-oxidant. The vinylidene compounds are prepared by dimerizing a 6 to 14 carbon alpha-olefin. These compositions are particularly useful under extreme conditions of temperature and/or reduced pressure as engine lubricants, hydraulic fluids, bases for greases, and the like. These olefinic dimers are prepared by coupling the vinylidene compounds in the presence of boron trifluoride complexed with a lower alkyl alcohol.

Recent years have seen an increasing demand for lubricants and other working fluids which are able to function satisfactorily at extreme conditions of temperature such as encountered in gas turbine engines and in aircraft jet engines. Not only must these high performance materials possess suitable viscosity properties to perform their intended function at temperatures above 350° F. and below −40° F., but in addition they must possess additional desirable characteristics which are required for continued use, including low volatility at the high temperatures encountered, relative inertness in an oxidizing environment, noncorrosiveness to the metallic and nonmetallic components contacted, and the like. The modern jet aircraft engines are particularly demanding in the severity of conditions encountered.

As aircraft jet engines are designed for and are used at increasingly more rigorous conditions including high operating temperatures and high altitudes, the specifications for the lubricants and related working fluids become more rigorous. Particularly demanding are the specifications relating to stability, evaporation loss, pour point and viscosity. The lubricant must meet specific requirements on viscosity over a wide temperature range if it is to function as a useful lubricant. It must possess an exceptionally low pour point so that cold engines can be started in northern winters and to permit sump storage at great altitudes without excessive thickening of the lubricant. It must be stable to decomposition at the high engine temperatures of modern jet engines and it must resist evaporation at the low pressures encountered at the high altitudes conventionally flown by these aircraft. For example, the viscosity specification for Type II jet turbine lubricants is determined from −40° F. to 400° F., and the evaporation loss is determined at 5.5 inches Hg. and 450° F. Type II jet turbine lubricant is used as a general term to refer to a class of materials which meets several closely related specifications. Pratt and Whitney Aircraft Corp. specification No. PWA 521-B and MIL-L-23699A are specifications for Type II aircraft jet engine lubricants. Although these specifications do not restrict the source of the lubricant, it has been found that naturally occurring materials from petroleum cannot meet the rigid specifications, therefore, synthetically prepared materials are required for jet engine and other high performance applications.

It is generally recognized that olefinic unsaturation must be eliminated from these high temperature lubricants. Olefinically unsaturated molecules have been found to be chemically unstable under the conditions at which the high temperature lubricant is normally used. This instability of olefins is due to the high reactivity of the olefinic double bond with atmospheric oxygen at the high operating temperatures in jet engines resulting in cleavage at the double bond and leading to acid groups on the molecular fragments. The cleavage of the molecules results in a reduction in the oil's viscosity while the acid groups resulting from the oxidation are highly corrosive to engine components. Those skilled in the field of extreme temperature lubricants have stated that synthetic hydrocarbon lubricants must be completely hydrogenated to provide oxidation and thermal stability for use as aircraft jet engine lubricants.

Notwithstanding the expressed requirement that olefinic unsaturation be avoided in high temperature lubricants, we have unexpectedly discovered an excellent synthetic lubricant that possesses an olefinic double bond in the molecule yet is as stable to degradation and oxidation, as determined by rigid specifications, as related molecular structures without olefinic unsaturation. We have discovered that the double bond in the molecule of our novel compound is substantially inert to degradation and oxidation as a result of the molecular structure and its position within the molecule. Any other location of the double bond in the molecule would subject it to easy oxidative attack. Our novel compound which includes a double bond located within the structure in the one position in which it is substantially free from attack, is made substantially quantitatively by our method of preparing it without significant contamination by undesired isomeric molecular structures which would be subject to oxidative attack. The resulting product is directly usable as a high temperature lubricant without requiring expensive hydrogenation or purification procedures.

It is known that 1-olefins and mixtures of 1-olefins can be dimerized in good conversion and selectivity to vinylidene compounds. For example, U.S. Pat. No. 2,695,327 discloses the dimerization of 1-olefins in the presence of a catalyst such as trialkyl aluminum. By this method, for example, 1-decene dimerizes to 2-octyl-1-dodecene. The vinylidene compound can then be easily recovered in good yield by a procedure which includes fractional distillation. This vinylidene compound can be further reacted using aluminum chloride as described in U.S. Pat. No. 3,576,898 to produce a material having a greater molecular weight than the vinylidene compound. The direct product of this second reaction is then hydrogenated and purified to remove substantial amounts of undesired structures which degrade its properties. Alpha-olefin oligomers which are produced by other processes are also hydrogenated for use as extreme temperature lubricants.

We have found that when 2-octyl-1-dodecene, the vinylidene dimer of 1-decene, is reacted in the presence of anhydrous aluminum chloride in nitromethane, not only tetramers of the 1-decene, but also substantial amounts of pentamer-like material are produced. The tetramers are a mixture of olefinic isomers having a substantial proportion of the olefinic unsaturation in side chains where it is readily attacked under oxidizing conditions. The pentamer-like material, which is evidence of significant isomerization and dealkylation or fragmentation during the reaction, effects a substantial increase in the viscosity of the tetramer product and is very difficult to remove from the tetramer product. We have also found the presence of a substantial amount of hydroxyl groups in the product of this method. The presence of hydroxyl groups in the molecule is undesired because hydroxyl tends to directly oxidize to the acid or dehydrate to olefin which can then cleave and oxidize to acid, as described. This olefinic isomerization and hydroxylation requires that the composition by hydrogenated to substantially remove this unsaturation and hydroxylation inherent in the process otherwise the resulting composition is unstable under oxidizing conditions. Consistent results were not obtained with repeated experiments by this method.

When prepared by the process described herein for dimerizing the vinylidene compound, the dimer of the vinylidene compound, that is, the tetramer of the 1-olefin, is routinely and consistently produced in substantially quantitative yield and substantially free of any pentamer. Furthermore, we have discovered that this novel dimer of the vinylidene compound, which is produced by this process is substantially quantitative yield, contains the double bond in a position within the molecule at which it is essentially free from degradation and oxidative attack. We have also found that this 1-olefin tetramer is substantially completely free of hydroxyl contaminant. Thus, we have determined that the process produces a sterically hindered 1-olefin tetramer, in substantially pure form, that is, it is free of unhindered isomers or other undesired molecular structures and is free of nontetramer products. This unsaturated 1-olefin tetramer as prepared by the process described herein is itself a novel composition of matter which unexpectedly is useful without hydrogenation desirably with a minor amount of a lubricating oil anti-oxidant as an extreme temperature lubricant such as in aircraft jet engines. The substantially pure, hydroxyl-free, unsaturated dimer of 2-octyl-1-dodecene produced by the process is 11,13-dioctyl-13-methyl-11-tricosene.

We have discovered that the process can be used as the second step in a two-stage dimerization process for producing substantially pure, unsaturated tetramers from 1-olefins having from about 6 to about 14 carbon atoms including olefins having an odd number of carbon atoms and mixtures of these 1-olefins. These starting 1-olefins can either be straight chain olefins or branched chain olefins provided that there is at least 1 hydrogen atom on the 2-carbon atom. The preferred starting olefins have from 8 to 12 carbon atoms. The most preferred olefins are 1-octene, 1-decene and mixtures of these.

The 1-olefin is dimerized by known methods and the vinylidene dimer is purified in a conventional manner. The vinylidene dimer of the 1-olefin which is the starting material in our process possesses the structural formula:

(1)

in which each R group is an alkyl group independently having from 4 to 12 carbon atoms. This vinylidene compound is dimerized by our process to produce a dimer of the vinylidene compound, which is a tetramer of the starting 1-olefin, having the structural formula:

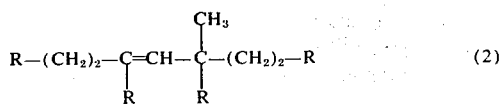

(2)

in which each R group is an alkyl group independently having from 4 to 12 carbon atoms as described above. In this formula and the formula (1) for the vinylidene compound each R group possesses two less carbon atoms than the starting olefin from which it originated. Thus, when 1-decene is the starting olefin, R— is $CH_3(CH_2)_7$—.

When the starting olefin is a mixture, such as a 50/50 molar mixture of 1-octene and 1-decene, R- is either $CH_3(CH_2)_5$— or $CH_3(CH_2)_7$—. The likelihood of an alkyl group occurring in any specific position is directly related to the molar proportion of the 1-olefin from which the group is derived in the initial olefin mixture. By substantially pure 1-olefin tetramer or substantially pure vinylidene dimer as used herein, we mean a reaction product consisting of one or more molecular species conforming with the above structural formula (2) and substantially free of molecular species which do not conform with the above structural formula (2). Therefore, a substantially pure mixture of 1-olefin tetramers conforming with structural formula (2) and varying only in the alkyl groups is produced when a mixture of 1-olefins is used to make the vinylidene dimer.

The catalyst which we have discovered to be required for the specific dimerization of the vinylidene compound of formula (1) to produce the 1-olefin tetramer in substantial purity as represented by the above structural formula (2) is boron trifluoride in a 1:1 molar complex with a lower alkyl alcohol, namely, methanol, ethanol, n-propanol, n-butanol, n-pentanol, n-hexanol, their branched chained isomers, such as isopropanol and the like, and mixtures of these alcohols. These $BF_3$·lower alcohol complexes are conveniently prepared by passing $BF_3$ gas through the liquid alcohol. When the alcohol stops absorbing $BF_3$, the formation of the 1:1 molar complex of the alcohol with $BF_3$ is completed. If the absorption of $BF_3$ is incomplete, a 1:2 molar $BF_3$ to lower alcohol can be produced. However, we have found the 1:2 $BF_3$·lower alcohol complex to be substantially inert for the desired dimerization reaction. The 1:1 molar complex will catalyze the reaction when mixed with the 1:2 molar complex, however, the latter is generally avoided as being of no particular advantage.

The molar ratio of $BF_3$·alcohol complex to vinylidene compound for the dimerization to the tetramer can conveniently be between about 0.01:1 to about 1:1 and preferably about 0.05:1 to about 0.2:1. The dimerization of the vinylidene compound can be successfully carried out using a molar ratio of $BF_3$·alcohol complex to vinylidene compound even broader than the above ratios but less effectively. In broad terms it is necessary to use a catalytic amount of $BF_3$·alcohol complex or an amount which is catalytically effective to dimerize the vinylidene compound.

The dimerization of the vinylidene compound using the $BF_3$·alcohol complex is carried out at moderate temperatures. The reaction can be carried out at a temperature of about −10° C. to about 200° C., preferably at a temperature between about 0° C. and about 150° C., and most preferably a temperature between about 30° C. and about 70° C.

The reaction vessel is preferably closed or separated from the atmosphere to keep moisture from contacting the $BF_3$·alcohol complex and interfering with its catalytic effectiveness. Pressure does not have a significant effect on the reaction, therefore, the reactor can conveniently be about atmospheric pressure or a lower or higher pressure if such is convenient, however, there is no advantage to excessively low or excessively high pressures.

As indicated, the herein described tetramer materials are prepared by the dimerization of vinylidene dimers of 1-olefins having from about six to about 14 carbon atoms. If a pure 1-olefin is used, the ultimate tetramer will be a compound having from about 24 to about 56 carbon atoms, depending on the starting olefin. If a mixture of 1-olefins is used, the tetramer product will be a mixture of isomers and homologs having a carbon number within the specified range. For example, the tetramer product obtained by the dimerization of a mixture of 1-octene and 1-decene and the dimerization of the resulting mixture of vinylidene compounds by the process as described herein will contain a mixture of olefinically unsaturated molecules including isomers having 32, 34, 36, 38 and 40 carbon atoms.

Although any composition coming within the above formula (2) for 1-olefin tetramers or mixtures thereof is stable as a lubricant against oxidative and other degradation, we have found that specific formulations are preferred to meet specific lubricant formulations. For example, we have found that about a 60:40 molar ratio of 1-octene to 1-decene produces a mixed tetramer product which is particularly effective in accordance with Pratt and Whitney Aircraft Corporation specification No. PWA 521-B for Type II jet engine lubricants.

The dimerization of the vinylidene compound in the presence of the $BF_3$ lower alkyl alcohol complex is time dependent. With increasing time the reaction rate decreases. At the time that the reaction is substantially completed or that further reaction is not desired, the catalyst is deactivated with a base such as by the addition of a sodium hydroxide solution. The organic product can be recovered and separated from the aqueous phase with water washing, decantation and/or vacuum distillation. Unreacted vinylidene compound, if any, and 1-olefin dimer impurities are separated by distillation. The resulting product is the tetramer of the initial 1-olefin substantially free of impurities which do not come within the above formula (2).

The dimerization of the 1-olefin to form the vinylidene compound is well described in the prior art. The dimerization is conveniently carried out at a temperature between about 60° C. and about 350° C., preferably about 100° to about 250° C. in the presence of a catalytic amount of a compound of a metal such as aluminum, gallium, indium and beryllium with monovalent aliphatic radicals, hydrogen or mixtures of these. We have found that this procedure for making the vinylidene compound consistently results in a dimer fraction comprising about 85 to about 90 percent or more of the desired vinylidene structure with the remainder being saturated dimer and an internal unsaturated dimer fraction which is substantially nonreactive in the second stage reaction. These 1-olefin dimer impurities can be removed from the tetramer product by distillation or other convenient separative procedure. The reaction to produce the tetramer as described herein can be substantially quantitative based on the vinylidene compound or compounds in the vinylidene feed mixture which have reacted. Regardless of the method of preparation of the vinylidene compound it is important that it be substantially free of any compound, including any compound of undesired carbon number which would result in an undesired fraction which would be difficult to separate from the desired tetramer product.

These olefinically unsaturated 1-olefin tetramer compositions as defined by formula (2) are directly usable as base stocks for engine lubricants or in other high temperature applications without requiring the considerable expense of hydrogenation. Not only is hydrogenation expensive due to the capital equipment and labor required, but also as a result of the significant reduction in ultimate yield occasioned by this additional processing step. Specific compositions coming within the broad class defined by structural formula (2) are able to meet the particular requirements of various specifications for jet engine lubricants. They are as stable against oxidation, cracking and other degradation as determined by Type II specifications, as the saturated composition corresponding with structural formula (2). When used as lubricants and hydraulic fluids in jet engines, and the like, conventional additives are added to provide specific properties as desired or as required by the specifications. A lubricating oil anti-oxidant is particularly advantageous for significantly enhancing the functional utility of the formulation. The additives comprise a minor proportion of the lubricant formulation, generally no greater than about 5 percent.

The substantially pure 1-olefin tetramer has been thoroughly characterized from the reaction mechanism and by infrared spectroscopy, nuclear magnetic resonance analysis, gas chromatography and vapor pressure osmometry. The infrared and nuclear magnetic resonance analysis identifies the location of the double bond and identifies other functional groups, if any. Gas chromatography establishes carbon number purity. Vapor pressure osmometry establishes the molecular weight of the product.

The following examples are set out to illustrate the novel compositions of the present invention and to provide a better understanding of its details and advantages.

EXAMPLE 1

Thirty cc. of ethanol are placed in a 100 ml. flask under a nitrogen atmosphere. The flask is placed in a wet ice bath to dissipate the 17K cal./mol of heat evolved in the reaction. $BF_3$ gas is introduced into the ethanol at a rate such that the heat of reaction can be controlled. The bubbling was reduced as $BF_3$ gas appeared at the vent and was stopped when it was no longer absorbed by the ethanol. The product was 0.51 mol of $BF_3$ and ethanol in a 1:1 molar complex.

EXAMPLE 2

Fifty grams of 2-octyl-1-dodecene were introduced into a 250 cc. flask under nitrogen at atmospheric pressure. The 2-octyl-1-dodecene was prepared by dimerizing 1-decene in the presence of triisobutyl aluminum. It analyzed 85.2 mol percent 2-octyl-1-dodecene, 7.1 percent 2-octyldodecane, and 7.6 percent $C_{20}$ internal olefins. The saturated compound was inert in the dimerization reaction and the internal olefins exhibited substantially no reactivity in the second dimerization reaction.

At room temperature (25° C.) 7.5 cc. of BF$_3$. ethanol complex was added to the flask. The solution immediately heated about 10° to 15° C. and additional heat was added to maintain a constant temperature of about 45° C. The mixture was continuously stirred for the full time of the reaction. The reaction was stopped after about 21.5 hours by the addition of about 2.5 cc. of a 10 percent sodium hydroxide solution and the stirring was continued. The hydrocarbon and aqueous layers were separated by decantation and the hydrocarbon oil was then vacuum distilled in a rotating disk molecular still at 120° C. and 50 microns pressure. This procedure separated unreacted 2-octyl-1-dodecene, the C$_{20}$ internal olefins and the 2-octyldodecane from the product. The yield of 11,13-dioctyl-13-methyl-11-tricosene was 71 percent based on the total feed and 83.3 percent based on the 2-octyl-1-dodecene in the feed. No compounds having more than 40 carbon atoms were detected in the product.

EXAMPLE 3

The previous example was repeated except that the reaction was carried out at a constant temperature of 67° C. for 21.5 hours. The yield of 11,13-dioctyl-13-methyl-11-tricosene was 70 percent based on the total feed and 82 percent based on the 2-octyl-1-dodecene in the feed.

EXAMPLE 4

Example 2 was repeated except that the reaction was carried out at a constant temperature of 101° C. for 22 hours. The yield of 11,13-dioctyl-13-methyl-11-tricosene was 63 percent, based on the total feed and 74 percent based on the 2-octyl-1-dodecene in the feed.

EXAMPLE 5

In the same procedures used in the preceding examples 400 grams of 2-hexyl-1-decene were mixed with 30 cc. of the BF$_3$. ethanol complex and the reaction was carried out at a constant temperature of 48° C. for 21.5 hours. The yield of 9-11-dihexyl-11-methyl-9-nonadecene was 77 percent based on the total feed and about 90 percent based on the 2-hexyl-1-decene in the feed.

EXAMPLE 6

A mixture of vinylidene dimers were prepared by dimerizing a 1-octene and 1-decene mixture containing 60 mol percent 1-octene using triisobutyl aluminum as the catalyst. After removing unreacted monomer, the mixture was determined to contain 31.9 weight percent of 16-carbon compounds, 47.1 percent of 18-carbon compounds and 21.0 percent of 20-carbon compounds by gas chromatographic analysis. A 6 kilogram portion of this mixture was introduced into a 12 liter resin-flask under a nitrogen atmosphere. The resin-flask was equipped with a thermometer, a heating mantle and a mechanical stirrer. Without supplemental heating, 450 cc. of a BF$_3$. ethanol complex was added to the flask. The temperature was maintained at 45° C. for 22 hours with stirring during reaction. The hydrocarbon and aqueous layers were separated by decantation following treatment of the reaction product mixture with aqueous sodium hydroxide. Unreacted C$_{16}$ to C$_{20}$ dimer was removed from the hydrocarbon portion by vacuum distillation in a rotating disk molecular still. The product was a mixture of unsaturated compounds having 32, 34, 36, 38 and 40 carbon atoms and conforming with structural formula (2) in which the R group was randomly either n-hexyl or n-octyl. This product was recovered in 76 weight percent yield based on the initial vinylidene mixture.

This tetramer mixture was compared with specification No. PWA 521-B according to Table I:

Table I

| | ASTM | PWA 521-B | Product |
|---|---|---|---|
| Viscosity | D445 | | |
| at −40°F., cs. | | 13,000 max. | 6,250 |
| at 100°F., cs. | | 100 max. | 29.7 |
| at 210°F., cs. | | 5.5 max. | 5.32 |
| at 400°F., cs. | | 1.0 min. | 1.31 |
| Viscosity index | | — | 124 |
| Pour Point, °F. | D97 | −75 max. | −95 |
| Specific Gravity | | — | 0.8335 |
| Refractive index | | — | 1.4657 |
| Evaporation loss after 6.5 hrs.% | D972 | | |
| at 29.9 in. Hg., 400°F. | | 25 max. | 14.0 |
| at 5.5 in.Hg., 450° F. | | 50 max. | 45.1 |
| Flash point, °F. | D92 | 400 min. | 420 |

The sample also passed the Pratt and Whitney rubber deterioration test (AMS-7280).

EXAMPLE 7

A vinylidene dimer mixture (7,523.6 grams) prepared from a mixture containing 60 mol percent 1-octene and 40 mol percent 1-decene was charged to a 12 liter pot under a nitrogen atmosphere. The BF$_3$. ethanol catalyst (376 cc.) was added with stirring over a 24 minute period. Stirring was continued while a reaction temperature of 45° C. was maintained for four hours. At the end of the four-hour period 1,500 cc. of distilled water was added to stop the reaction. The hydrocarbon phase was washed with water until the wash water was neutral. The tetramer product, separated from the unreacted vinylidene reaction mixture, was obtained in 65.7 percent yield based on the total feed to the reactor. The mixture of tetramer isomers and homologs was compared with MIL-L-23699 specification for Type II jet engine lubricants.

Table II

| Viscosity | MIL-L-23699 | Product |
|---|---|---|
| at −40° F., cs. | 13,000 max. | 5,861 |
| at 100° F., cs. | 25 min. | 29.0 |
| at 210° F., cs. | 5.0 to 5.5 | 5.25 |
| at 400° F., cs. | — | 1.30 |
| Pour point | −65° F., max. | −90° F. |
| Flash point | 450 min. | |
| Acid No. | — | 0.04 |
| Evaporation loss,% after 6.5 hours | | |
| at 29.9 in.Hg., 400° F. | 10.0 max. | 7.2 |

EXAMPLE 8

A tetramer product was made using the same procedure described in Example 6 starting with 8,296 grams of the vinylidene mixture and 415 cc. of the BF$_3$. ethanol catalyst at 45° C. for 20 hours. The product containing homologous and isomeric olefin tetramers with molecular weights of 32, 34, 36 38 and 40 and conforming with structural formula (2) was obtained in 70 percent yield based on the initial mixture containing the vinylidene compounds. The pale straw-yellow tetramer product mixture was clay treated by passing it through a column of attapulgus clay to remove any impurities conventionally removed by clay treating. The tetramer product was made water white by this treatment. The specifications for the product before and after clay treating are set out in Table III.

Table III

| Viscosity | Before Clay Treating | After Clay Treating |
|---|---|---|
| −40° F., cs. | 6991 | 6906 |
| 100° F., cs. | 31.0 | 31.05 |
| 210° F., cs. | 5.46 | 5.48 |
| 400° F., cs. | 1.33 | 1.33 |
| Viscosity index | 124 | 124 |
| Pour point, °F. | −95 | −95 |
| Evaporation loss at 29.9 in.Hg., 400° F. | 11.3 | 10.4 |

EXAMPLE 9

Five 50 gram samples of the vinylidene mixture made from a 60 mol percent 1-octene -40 mol percent 1-decene mixture in the manner described in Example 2 were separately treated with 10, 5, 2.5, 1.0 and 0.5 cc. of $BF_3$. ethanol complex for 21.5 hours at 45° C. The yields of the mixture of the tetramers conforming with structural formula (2) from each of the five samples of vinylidene mixture were 73, 74, 73, 48 and 22 weight percent, respectively, based on the vinylidene reaction mixture.

EXAMPLE 10

Three 50 gram samples of the vinylidene mixture as described in Example 9 were reacted at 0° C., 45° C., and 70° C. for 22, 21.5, and 21.5 hours, respectively, using 2.5 cc. of $BF_3$. ethanol complex with each sample. The yields of the tetramers conforming with structural formula (2) from each of the three samples was 67, 73 and 65 weight percent, respectively, based on the vinylidene reaction mixture.

EXAMPLE 11

A tetramer product was made from a vinylidene mixture which was prepared from a mixture of 70 mol percent 1-octene and 30 mol percent 1-decene as described in Example 2. A 300 gram sample of the vinylidene mixture and 22.5 cc. of $BF_3$. ethanol complex were reacted at 45° C. for 21.5 hours. The yield of tetramer product mixture conforming with structural formula (2) was 69 percent based on the vinylidene reaction mixture. The tetramer product mixture had a viscosity of 6,148 cs. at −40° F., 28.95 cs. at 100° F., 5.21 cs. at 210° F., and 1.29 cs. at 400 °F., and a pour point of −85° F.

EXAMPLE 12

A tetramer product was made by reacting 26.3 cc. of a $BF_3$. ethanol complex with 175 grams of a vinylidene mixture, obtained from a mixture of 1-octene ad 1-decene, containing 43.8 weight percent of 16-carbon compounds, 45.2 percent 18-carbon compounds and 11.0 percent 20-carbon compounds. The reaction was carried out at 45° C. for 21 hours. The tetramer product conforming with structural formula (2) was 72 percent based on the vinylidene mixture and it possessed a 210° F. viscosity of 5.46 cs.

EXAMPLE 13

A vinylidene mixture containing 16-, 18-, and 20-carbon vinylidene compounds was made from a 50/50 molar mixture of 1-octene and 1-decene. A 600 gram portion of this vinylidene mixture was dimerized in the presence of 45 cc. of $BF_3$. ethanol complex at a temperature of 49° C. for 21.5 hours. The reaction yielded 73 weight percent of the tetramers defined by structural formula (2) based on the total vinylidene mixture reacted.

EXAMPLE 14

The 18-carbon fraction was fractionated from a vinylidene mixture which had been prepared from a mixture of 70 mol percent 1-octene and 30 mol percent 1-decene. Seventy-five grams of this 18-carbon fraction were dimerized in the presence of 11.2 cc. of $BF_3$. ethanol complex at 45° C. for 21.5 hours. The yield of 36-carbon tetramer isomers was 74 percent based on the vinylidene reaction mixture. The product had a 210° F. viscosity of 5.86 cs.

EXAMPLE 15

In like manner Example 14 was repeated using 26.3 cc. of $BF_3$. ethanol complex and 175 grams of the 18-carbon fraction fractionated from the vinylidene mixture. The yield of the tetramer isomers was 74 percent based on the vinylidene feed mixture. The isomer mixture exhibited at 210° F. viscosity of 5.69 cs.

EXAMPLE 16

A 1:1 complex of boron trifluoride and n-butanol was prepared by bubbling boron trifluoride into n-butanol. The introduction of the boron trifluoride was stopped after the reaction to the 1:1 $BF_3$. butanol complex was completed. Three 50 gram portions of a vinylidene dimer mixture prepared from a 50/50 mixture of 1-octene and 1-decene were separately dimerized in the presence of 4.21 g., 2.11 g. and 1.40 g., respectively, of the $BF_3$. n-butanol complex at 45° C. for 21.5 hours. The yields of product conforming with structural formula (2) and based on the vinylidene reaction mixture were 69, 36 and 14 percent, respectively.

EXAMPLE 17

Two 50 gram portions of the vinylidene mixture prepared from a mixture containing 60 mol percent 1-octene and 40 mol percent 1-decene were separately dimerized in the presence of 2.5 g. and 1.9 g. of the $BF_3$. n-butanol complex at 45° C. for 22 and 22.5 hours, respectively. The yields of product tetramer conforming with structural formula (2) were 70 and 34 percent, respectively, based on the vinylidene reaction mixture.

EXAMPLE 18

Four 50 gram portions of a vinylidene mixture prepared by dimerization from a mixture containing 50 mol percent 1-octene and 50 mol percent 1-decene were separately dimerized in the presence of 4.63 g., 3.24 g., 2.32 g., and 1.53 g. of a $BF_3$. n-pentanol complex at a temperature of 45° C. for 21.5, 21.5, 22 and 22 hours, respectively. The yields of tetramer product conforming with structural formula (2) were 69, 56, 29 and 12 weight percent, respectively, based on the vinylidene mixture used.

EXAMPLE 19

Fifty grams of the vinylidene mixture used in the preceding example was dimerized in the presence of 5.04 grams of a $BF_3$. n-hexanol complex at a temperature of 45° C. for 21.5 hours. The yield of tetramer product conforming with structural formula (2 ) was 70 weight percent based on the vinylidene reaction mixture.

EXAMPLE 20

A 4,629 gram portion of the vinylidene dimer mixture from 1-decene as described in Example 2 was dimerized in the presence of 240 cc. of $BF_3$. ethanol complex at a temperature of 51° C. for 22.5 hours. The yield to 11,13-dioctyl-13-methyl-11-tricosene was 73 weight percent based on the feed mixture. The viscosity of the tetramer was 6.67 cs. at 210° F.

EXAMPLE 21

Example 20 was repeated except that 10 kilograms of the vinylidene dimer were dimerized in the presence of 500 cc. of $BF_3$. ethanol complex for 23 hours. The yield of 11,13-dioctyl-13-methyl-11-tricosene was 74 weight percent based on the feed mixture. This product was compared with Ford Motor Company specifications for primary mover turbine oils.

Table IV

| Viscosity | Ford Spec. | Product |
|---|---|---|
| at −40° F., cs. | 18,000 max. | 11,800 |
| at 0° F., cs. | 2,000 max. | 965 |
| at 100° F., cs. | 20 min. | 39.55 |
| at 210° F., cs. | 5.0–7.0 | 6.69 |
| at 300° F., cs. | — | 2.90 |
| at 325° F., cs. | 2.0 min. | 2.45 |
| at 400° F., cs. | — | 1.56 |
| Viscosity index | — | 130 |
| Pour point, °F. | −20 max. | −65 |
| Flash point, open cup, °F. | 425 min. | 515 |
| Fire point, open cup, °F. | 450 min. | 555 |
| Total acid number | 0.5 max. | 0.03 |
| Evaporation loss, % $N_2$ atm., 22 hrs., 300° F. | 2.0 max. | 0.40 |

EXAMPLE 22

2-Butyl-1-octene was prepared by dimerizing 1-hexene in the presence of triisobutyl aluminum. After removing unreacted 1-hexene, the product analyzed about 85 percent 2-butyl-1-octene with the remainder being 2-butyloctane and 12 carbon internal olefins. A 150 gram portion of the 2-butyl-1-octene product was dimerized in the presence of $BF_3$. n-butanol complex for 22 hours at 45° C. After washing and separating out the 12 carbon hydrocarbons, the 7,9-dibutyl-9-methyl-7-pentadecene product was subjected to analysis. The infrared spectra revealed that the product possessed only one type of double bond with no unhindered double bond detected and further showed that no hydroxyl group was present in the product. Nuclear magnetic resonance spectroscopy revealed that there was only one type of double bond present in the product and that only one proton was present on the double bond. Gas chromatography and vapor pressure osmometry verified the carbon number of the product at 24.

The tetramer produced from 2-hexyl-1-dodecene in other experiments showed similar spectra at reduced intensity. In many dozens of experiments using a vinylidene dimer of a 1-olefin and a $BF_3$. alcohol complex as described herein, we obtained consistent results including yield of product with no showing of trimer or pentamer of the initial olefin.

EXAMPLE 23

The reaction was carried out in a 500 ml. four-necked flask equipped with a stirrer, a thermocouple and a nitrogen bubbler. After purging the reaction flask for 24 hours with dry nitrogen, 100 ml. of nitromethane was first added and then 13.3 grams of aluminum chloride was added with stirring while maintaining the reactor's contents at 5° C. in an ice bath. After solution was obtained, a 168 gram portion of 2-butyl-1-octene, as described in the preceding example, was slowly added over a period of 30 minutes at 3° to 5° C. After addition of the dimer was completted, the temperature was maintained at a temperature of 5° C. with stirring for 3.5 hours.

The mixture was then poured into 500 ml. of water followed by 100 ml. of hexane. The organic layer was washed in succession with 500 cc. of water, 500 cc. of 10 percent HCl in water, 500 cc. of 10 percent NaOH in water and 500 cc. water. The organic phase was then separated out, filtered and distilled to remove hexane and 12 carbon compounds.

The resulting product was 95.7 grams of a 24-carbon tetramer cut boiling at 162° C. at 1 mm. Hg, and having a refractive index of 1.4556. The bottoms fraction of 36.8 grams was indentified as a tetramer-pentamer mixture by gas chromatography. The yield of tetramer and pentamer based on the dimer feed material was 78.9 percent with about seven percent being pentamer.

The product was subjected to infrared spectroscopy and found to have a strong showing of hydroxyl groups and a strong carbon to carbon double bond showing in an unhindered position. Nuclear magnetic resonance analysis disclosed double bond in the product with two protons on the double bond and four protons on carbon adjacent to the double bond with no showing (80 percent limit of detection of a double bond with only one proton on the double bond.

EXAMPLE 24

Example 23 was repeated except that 277.7 grams of the 20-carbon vinylidene compound mixture prepared from 1-decene as described in Example 2 was introduced into the reactor instead of the 1-hexene dimer. A product was obtained which analyzed by gas chromatographic analysis as about nine percent 1-decene trimer, about 31 percent 1-decene tetramer and at least about one percent 1-decene pentamer. The infrared and nuclear magnetic resonance spectra of this product were similar to those described in the preceding example at reduced intensity. This experiment was duplicated several times with erratic results including lower yields than described in this example.

EXAMPLE 25

A 50 gram portion of a 1-decene dimer as described in Example 2 was placed in a 100 ml. flask under a nitrogen atmosphere. A 1:1 $BF_3$. diethyl ether complex was made from diethyl ether which had been purified from ketone, aldehyde, peroxide and alcohol and five cc. were added to the flask. A temperature of 45° C. was maintained on the contents of the flask by a heating mantle. After 21.5 hours the contents of the flask were analyzed showing a yield to tetramer of less than 1 percent.

The olefinically unsaturated tetramer or tetramer mixture that is produced from a 1-olefin or 1-olefin mixture by the two-step procedure described herein possesses a number of properties including very low pour point, very low volatility, low low-temperature viscosity and high oxidation stability which make it particularly suitable as a functional fluid in a wide variety of applications involving rigorous conditions. Representative examples of these applications include the following uses: high temperature gas turbine lubricant, hydraulic fluids for aircraft and arctic applications, general lubricant for space vehicles, vacuum pump lubricant, sealed-for-life drive train lubricant, hydraulic fluid temperature applications such as in steel mills, low temperature instrument lubricant, and the like.

Notwithstanding the high stability of the 1-olefin tetramer base stock the addition of an oxidation-corrosion inhibitor to the tetramer is of particular advantage for all uses of the tetramer since these inhibitors are generally known to have their maximum beneficial influence when the unmodified base stock is itself highly stable. Other additives are optionally useful for particular applications of the tetramer product including detergent-dispersants, antifoam agents, anti-wear agents, swelling and anti-swelling agents, and the like. The additives are used in a total amount of the additive portion of about 0.1 to about 10 weight percent and preferably about 0.5 to about 5 weight percent of the compounded tetramer product, with each additive being used in an amount designed to obtain maximum benefits.

Since a decrease in the oxidation of a lubricant or hydraulic fluid results in a decrease in the corrosion of metals contacted by these materials, and since an additive which can passivate a metal surface acts indirectly as an anti-oxidant by neutralizing the metal catalyst, the various oxidation and corrosion inhibitors possess both properties in varying degrees. For these reasons the oxidation and corrosion inhibitors are designated herein by the general term anti-oxidant for convenience.

The various anti-oxidants which are effective anti-oxidants in lubricating oils and which are soluble in the tetramer can be used in formulating the compounded tetramer product. A description of anti-oxidant function and types is found in *Motor Oils and Engine Lubrication* by Alphonse Schilling, Scientific Publications (G.B.) Ltd. (1968). The conditions to which the functional fluid will be subjected and the system in which it is used will affect the selection of an anti-oxidant which will provide optimum results. For example, the compounded tetramer will be used in contact with one or more metals; including iron, copper, lead, cadmium, silver and the like, which will be found in engine parts, sumps, pumps, tubing, bearings, soldered or welded joints and the like, with each particular metal combination dictating a preferred group of anti-oxidants. Some of the problems minimized or eliminated by the anti-oxidants are fouling from lower molecular weight lacquer deposits or higher molecular weight varnish-like polymer deposits, corrosion of metal parts, bearing degradation by corrosion, the formation of sludges, and the like.

Typical useful anti-oxidants include
N,N,N',N'-tetramethyl-3,3'-diaminodiphenylmethane;
3,3'-di-n-octyldiphenylamine; phenyl-1-naphthylamine; phenyl-2-naphthylamine; 1,2,3-benzotriazole and its alkyl and phenyl substituted derivatives; 1,4-dihydroxylanthraquinone; 2,6-di-t-butyl-p-cresol; 4,4'-methylene-bis(2,6-di-t-butylphenol); 2,2'-methylene-bis(4-methyl-6-t-butylphenol); metal dialkyldithiocarbamates in which the alkyl group contains three to eight carbon atoms such as zinc di-n-propyldithiocarbamate; and the like or mixtures thereof. A preferred anti-wear agent is tricresylphosphate. Typical ashless-type, detergent-dispersants, which are useful, are the N-substituted long chain alkenyl succinimides obtained by the condensation of a polyisobutylene having a molecular weight of about 800–1200 with maleic anhydride and then reacted with a polyalkyleneamine such as triethylenetetramine; and the like. A suitable anti-foam agent such as polydimethylsiloxane can also be used if desired. In view of the very low inherent pour point of the 1-olefin tetramer, a pour point depressant not only is not necessary, but probably would have no beneficial effect.

We have surprisingly discovered an unexpected property and advantage of the unsaturated tetramer material over its hydrogenated counterpart which enhances its utility. We have found that the unsaturated tetramer will swell seals more effectively than the saturated tetramer thereby minimizing the need of a special additive for this purpose. Also the unsaturated tetramer will dissolve and disperse deposits occurring at hot spots in the system more effectively than the saturated tetramer, thereby avoiding disruptive system blockages. Both of these benefits result from superior solvent properties in the unsaturated tetramer.

EXAMPLE 26

A portion of a 40-carbon tetramer of 1-decene was tested for corrosiveness and oxidation stability on magnesium metal by Federal Test Method Standard No. 791B with no additives. This tetramer was the unsaturated product made by the procedure such as described in Example 2. According to this test procedure five one-inch square pieces of magnesium were submerged in the tetramer and heated at 347° F. for 72 hours. At the end of the test period the weight loss of magnesium was determined to be 25.4 mg./in$^2$.

EXAMPLE 27

The procedure of Example 26 was repeated except that the unsaturated tetramer of 1-decene was modified with 3 percent by weight of additives. These additives were one percent each of technical grade dioctyldiphenylamine, and technical grade phenyl α-naphthylamine as anti-oxidants, one percent of tricresyl phosphate as an anti-wear agent and 0.033 percent of a silicone anti-foam agent. The magnesium squares exhibited an overall weight gain following the test of 0.02 mg./in$^2$.

EXAMPLE 28

The procedure of Example 27 was repeated except that 0.05 percent benzotriazole was included as an anti-oxidant together with the other additives. The magnesium squares resulting from the test showed a weight loss of 0.46 mg./in$^2$.

EXAMPLE 29

The test procedure of Example 26 was repeated at 425° F. for 48 hours using the unsaturated tetramer mixture prepared in the two-step procedure as described herein from a 60/40 molar mixture of 1-octene and 1-decene. To this unsaturated tetramer mixture were added one percent technical grade dioctyldiphenylamine, 0.05 percent benzotriazole and two percent 2,2'-methylene-bis(4-methyl-6-t-butylphenol) as anti-oxidants. Also added were 3 percent tricresyl phosphate and 0.033 of the silicone anti-foam agent. The tested magnesium squares showed a weight loss of 0.08 mg./in².

It is to be understood that the above disclosure is by way of specific example and that numerous modifications and variations are available to those of ordinary skill in the art without departing from the true spirit and scope of the invention.

We claim:

1. In a composition of matter comprising a major proportion of an oil of lubricating viscosity and a minor portion of conventional lubricating oil and hydraulic fluid additive in an amount sufficient to effect each additive attendant function including at least one lubricating oil antioxidant; the improvement comprising using as the base oil a composition of the formula

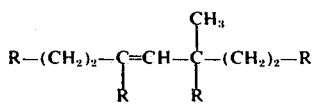

wherein each R group is a saturated alkyl group independently having from about 4 to about 12 carbon atoms.

2. The composition of matter in accordance with claim 1 in which each R group is a saturated normal alkyl group independently having 6 or 8 carbon atoms.

3. The composition of matter in accordance with claim 1 in which each R group is a saturated normal alkyl group having 8 carbon atoms.

4. The composition of matter in accordance with claim 1 in which each R group is a saturated normal alkyl group having 6 carbon atoms.

5. The composition of matter in accordance with claim 1 in which the additive component includes at least one member selected from anti-wear agents, dispersing agents and anti-foaming agents.

6. The composition of matter in accordance with claim 1 in which the additive component includes an anti-wear agent.

* * * * *